United States Patent
Meletiou, Jr.

(10) Patent No.: US 10,192,320 B2
(45) Date of Patent: Jan. 29, 2019

(54) DENTAL METHOD OF SMILE DESIGN

(71) Applicant: Demetrios S. Meletiou, Jr., Davidson, NC (US)

(72) Inventor: Demetrios S. Meletiou, Jr., Davidson, NC (US)

( * ) Notice: Subject to any disclaimer, the term of this patent is extended or adjusted under 35 U.S.C. 154(b) by 0 days.

(21) Appl. No.: 14/215,519

(22) Filed: Mar. 17, 2014

(65) Prior Publication Data

US 2014/0342304 A1    Nov. 20, 2014

Related U.S. Application Data

(60) Provisional application No. 61/793,323, filed on Mar. 15, 2013.

(51) Int. Cl.
| | |
|---|---|
| *A61C 13/00* | (2006.01) |
| *G06T 7/30* | (2017.01) |
| *G06K 9/62* | (2006.01) |
| *G06K 9/00* | (2006.01) |

(52) U.S. Cl.
CPC .............. *G06T 7/30* (2017.01); *G06K 9/6206* (2013.01); *G06K 9/00281* (2013.01); *G06T 2207/10004* (2013.01); *G06T 2207/10028* (2013.01); *G06T 2207/30036* (2013.01)

(58) Field of Classification Search
CPC ..... A61C 13/0004; G06T 7/30; G06K 9/6206
See application file for complete search history.

(56) References Cited

U.S. PATENT DOCUMENTS

| | | | |
|---|---|---|---|
| 8,352,060 B2* | 1/2013 | Chun | A61C 11/00 700/118 |
| 8,376,745 B2* | 2/2013 | Stonisch | A61C 19/10 433/215 |
| 8,454,365 B2* | 6/2013 | Boerjes | A61B 5/4547 433/223 |
| 8,545,221 B2* | 10/2013 | Stone-Collonge | G06F 19/3437 433/24 |
| 2013/0218530 A1* | 8/2013 | Deichmann | A61C 13/0004 703/1 |

* cited by examiner

*Primary Examiner* — Ralph Lewis
(74) *Attorney, Agent, or Firm* — Ronald L. Hofer

(57) ABSTRACT

A patient's smile is improved by photoimaging the patient's smile and scanning the patient's anterior teeth and associated soft lip structure to obtain sets of data mapping the patient's anterior teeth and associated soft tissue structure. The photo image is used to create a desired smile image which is then used to amend the data map of anterior teeth to a substantially identical resultant image which is then used to mill temporary and permanent prosthesis.

5 Claims, 1 Drawing Sheet

DENTAL METHOD OF SMILE DESIGN

FIELD OF THE INVENTION

The present invention relates to restorative orthodontic procedures. More particularly, the present method relates to a method of dental treatment for improved appearance and function.

BACKGROUND OF THE INVENTION

As dental technology has advanced, improvements have been made not only in methods for treating clinical dental conditions but also in methods for improving the esthetic appearance of patients' teeth and the appearance of a patient's smile. Conventional methods for improving a patient's appearance involve orthodontic procedures and/or restorative procedures to change the position, size and/or contour of one or more teeth.

Many patients have a particular concern about their appearance when smiling and there is increasing focus on "smile design" methods and procedures. Some patients have suffered damage to one or more teeth which require restoration. Other patients would like to improve the appearance of their natural teeth. Improving a patient's appearance, however, is often a challenging task requiring expertise in both art and science. For example, it has proven difficult to restore or improve smiles of patients who have spaces between teeth. Often times, in order to close a space between teeth, an inordinately wide tooth is created which throws off the harmony of its relationship to adjacent teeth and gums. There may also be issues between patients and their friends and/or family members because the esthetic appearance of a smile is subjectively determined. What is attractive or looks aesthetically pleasing to one person may not be attractive or look aesthetically pleasing to another person. Of course, where the objective is to improve the appearance of a patient's smile, the subjective aspect of the result is of great importance to the patient.

Accordingly, the present invention provides a method of improved smile design which uses advanced science but also fully takes into consideration the subjective nature of the intended result. Further understanding of the method of the present invention will be had from the following specification and claims taken in conjunction with the accompanying drawings.

SUMMARY OF THE INVENTION

In accordance with the present invention, a patient's smile is improved by a method comprising steps of:
(A) creating a photoimage of a patient's smile;
(B) creating a data map of the patient's anterior and associated soft tissue lip structure
(C) creating a desired smile image by manipulating the image of the patient's smile;
(D) amending the data map based on the desired smile image to create an image of the patient's smile which is substantially similar to the patient's proposed smile image using the amended datamap of the patient's anterior teeth with the datamap of the patient's soft tissue lip structure superimposed thereon;
(E) making a temporary prosthesis using the amended datamap;
(F) preparing the anterior teeth of the patient;
(G) installing the temporary prosthesis;
(H) testing the temporary prosthesis and making any desired adjustments to the amended datamap;
(I) making a permanent prosthesis; and
(J) installing the permanent prosthesis.

DETAILED DESCRIPTION OF THE PREFERRED EMBODIMENTS

Figure 1:
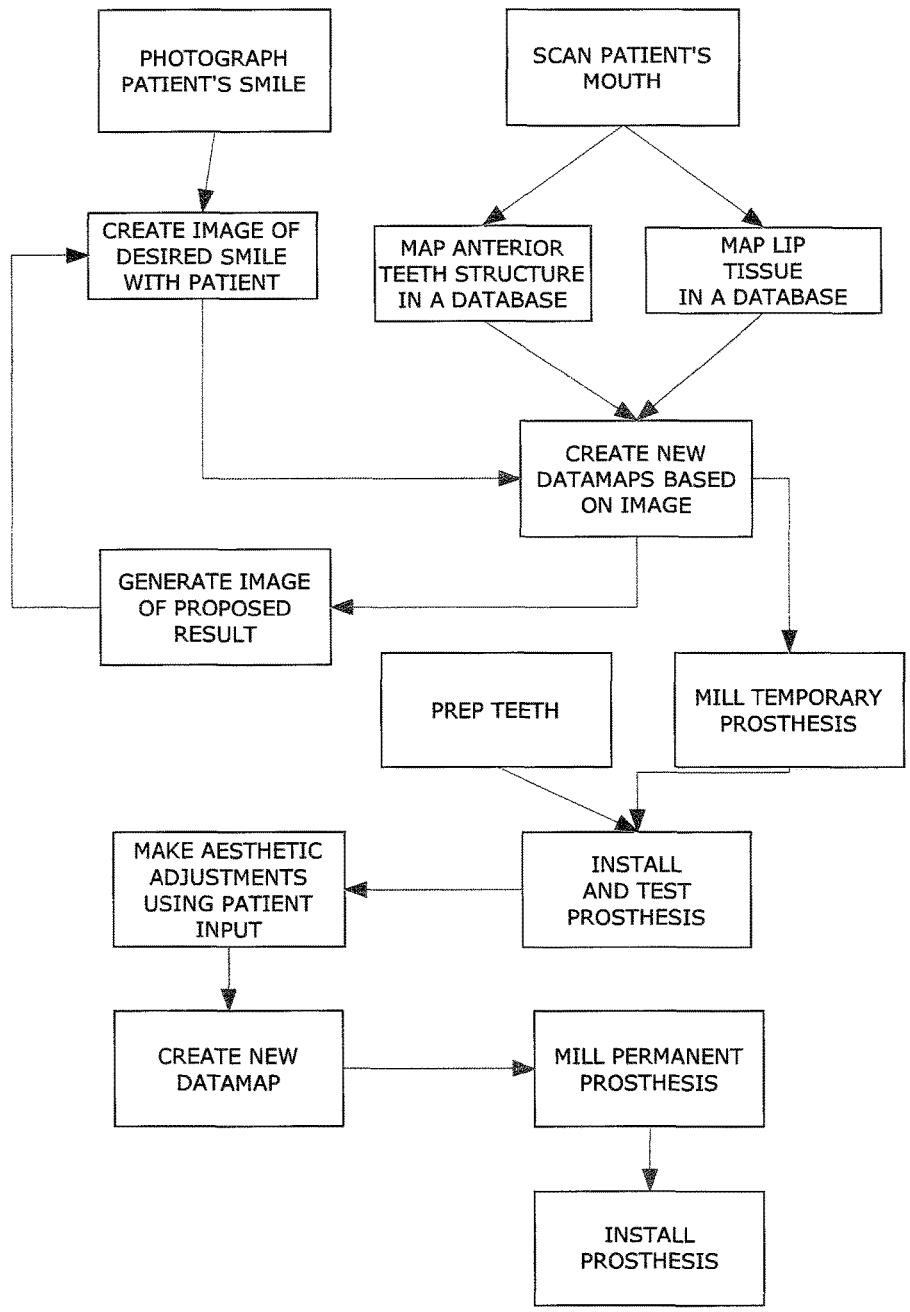
FIG. 1 is a block diagram illustrating the general steps of a preferred embodiment of the method of the present invention.

In accordance with the method of the present invention, imaging techniques in combination with computer aided design and milling techniques are used to improve a patient's smile. The method can be used to create a harmonious smile and, more importantly, can be used to create a smile which is made to the patient's subjective criterion.

The present method allows a dentist to accurately determine the appropriate size and shape of the 6 anterior teeth to improve the appearance of a patent's anterior teeth and smile. Anterior teeth generally comprise the set of 6 teeth known as: left canine, left lateral incisor, left central incisor, right central incisor, right lateral incisor and right canine. As is well appreciated by those skilled in the art, it is difficult to improve a patient's smile, especially when there are few landmarks to go by and appearance is to some extent a subjective standard. The method of the present invention facilitates subjective input from the patient or even patient's friends or family and is well adapted to use the well known "golden proportions" or "golden percentages" to obtain an attractive appearance.

It is contemplated that the method of the present invention will be carried out using a digital computer to create a proposed digitally enhanced smile and that the patient will be able to view the intended result prior to embarkation upon the treatment so that the patient can accept or make changes to the intended result before the prosthesis is milled and teeth are prepared for installation of the prosthesis. Visualizing the end result allows for increased patient acceptance and satisfaction and increases the chances that the patient's objectives and desires are achieved. Furthermore, the visualization of the intended result creates a framework for a dental lab to create the prosthesis. This will enhance doctor-laboratory communications to create a result most like that which was proposed to and accepted by the patient.

Now referring to FIG. 1, the general steps of a preferred embodiment of a method of the present invention are described therein in block diagram format. The method begins with the step of evaluating the patient's smile. Preferably this step is carried out by creating a photo image of the patient's smile and reviewing the image with the patient to determine or propose an end result. The end result may be based upon earlier photographs of the patient showing a smile that the patient found pleasing or may be based upon an artistic rendition of a smile which the patient would like to have. The desired image can be created using computer aided design or Photoshop techniques which are well known in the art and are readily commercially available. A smile catalog can be used to give the patient and dentist latitude to design a smile shape.

The aesthetic appearance of the anterior teeth and surrounding facial structure make up the appearance of the patient's smile. Thus, in order to carry out the steps of the present method, it is necessary to map the surfaces of the anterior teeth. It is contemplated that this step will be carried out by scanning the patient's anterior teeth to provide a database mapping the surfaces of the anterior teeth. It is also contemplated that a scan will also be taken of the soft tissue structure proximate to the anterior teeth. The data of these mapping steps can be further supplemented by particular parameters of tooth size such as incisal widths and lengths.

Suitable apparatus for making the data maps by scanning include: beam scanners and are commercially available from 3M, Lava and E4D.

The data results of the scans are stored in first and second databases respectively.

An alternative, but less desirable, mapping method can be carried out by using a suitably modified digital SLR camera preferably using a ring flash to provide additional data. The data points provide three axis location of the surface of each tooth and, provide the digitized data set necessary for computer processing of the data to obtain a visual image of the desired improvement in tooth or smile appearance.

The databases are used to create a proposed photo image which can be compared to the photo image of the desired result and reviewed by the patient. Adjustments to the image can be readily made on the computer and images can be repeatedly adjusted until the patient has the exact image desired. Any adjustments desired are made by manipulating the image on the computer to thereby adjust both the appearance of the image and also the map of the data in the computer. Where the data is changed, the computer can be used to calculate new measurements of each tooth or the data for one tooth can be changed without adjusting the data for other teeth.

Once the desired image is fixed, a temporary prosthesis can be milled using the database which has been adjusted to the fixed image and the dentist can proceed to prep the patient's teeth. The temporary prosthesis can be milled in the dentist's office using CAD milling apparatus. Suitable apparatus are commercially available. Alternatively, the data can be sent to a dental laboratory for their use in milling the prosthesis using computer aided milling equipment.

The dentist then installs a temporary prosthesis on the patient's teeth to provide a time period for the patient to evaluate the temporary result. Any changes desired to the result can then be communicated to the dentist and used to adjust the database and adjusted photo image generated and reviewed by the patient to obtain the precise result desired by the patient.

Once a final image has been confirmed, the database so modified is used to mill the permanent prosthesis which is then installed by the dentist.

It will be appreciated by those skilled in the art that while a detailed description of one embodiment of a method of this invention is described below, the present method is subject to variation and/or modification within the general steps set forth herein and that such variation and/or modification is intended to be within the broad scope of the present invention which is intended to be limited only by the following claims.

What is claimed is:

1. A method for improving the smile of a patient, the method comprising the steps of:
    making a desired photoimage of a patient's smile while creating computer datamaps of the patient's anterior teeth and associated soft tissue lip structure;
    using the desired photoimage to amend the datamap of the patient's anterior teeth and then using the amended datamap to create a second photoimage of the patient's proposed smile using the amended datamap with soft tissue lip structure superimposed thereon;
    making any desired adjustments to the second photoimage and using the adjusted second photoimage to further change said amended datamap;
    computer aided milling a temporary prosthesis using the amended datamap;
    preparing the anterior teeth of the patient;
    installing the temporary prosthesis on the patient;
    testing the temporary prosthesis and making any desired adjustments to the amended datamap;
    making a permanent prosthesis; and
    installing the permanent prosthesis.

2. The method of claim 1 wherein said milling step is carried out in a dentist's office.

3. The method of claim 1 wherein adjustments to said second photoimage are made using the patient's input.

4. The method of claim 1 wherein adjustments are made to said amended datamap which is then used to mill a permanent prosthesis.

5. A method for improving the smile of a patient, the method comprising the steps of:
    photoimaging a patient's smile to make a first image thereof;
    mapping the patient's anterior teeth structure to make a datamap thereof in a first database;
    mapping the patient's associated soft tissue lip structure to make a datamap thereof in a second database;
    making a desired smile image by manipulating said first image;
    using the desired smile image to make an amended datamap of the patient's anterior teeth;
    creating a proposed image of the patient's proposed smile using the amended datamap with soft tissue lip structure superimposed thereon;
    making any desired adjustments to the proposed image and changing the amended datamap to reflect the adjustments in a new datamap;
    computer aided milling a temporary prosthesis using the new datamap;
    preparing the anterior teeth of the patient;
    installing the temporary prosthesis on the patient;
    testing the temporary prosthesis and making any desired adjustments to the new datamap;
    making a permanent prosthesis using the adjusted new datamap; and
    installing the permanent prosthesis on the patient.

* * * * *